(12) United States Patent
 Ko

(10) Patent No.: US 9,744,371 B2
(45) Date of Patent: *Aug. 29, 2017

(54) TREATMENT APPARATUS USING HIGH FREQUENCY WAVES AND METHOD FOR CONTROLLING SAME

(71) Applicant: Lutronic Corporation, Gyeonggi-do (KR)

(72) Inventor: Kwang Chon Ko, Gyeonggi-do (KR)

(73) Assignee: Lutronic Corporation, Gyeonggi-do (KR)

( * ) Notice: Subject to any disclaimer, the term of this patent is extended or adjusted under 35 U.S.C. 154(b) by 0 days.

This patent is subject to a terminal disclaimer.

(21) Appl. No.: 15/167,467

(22) Filed: May 27, 2016

(65) Prior Publication Data

US 2016/0271410 A1    Sep. 22, 2016

Related U.S. Application Data

(63) Continuation of application No. 14/234,864, filed as application No. PCT/KR2012/005848 on Jul. 23, 2012, now Pat. No. 9,364,392.

(30) Foreign Application Priority Data

Jul. 26, 2011    (KR) ........................ 10-2011-0074202

(51) Int. Cl.
*A61N 1/00*       (2006.01)
*A61B 5/02*       (2006.01)
(Continued)

(52) U.S. Cl.
CPC .............. *A61N 1/40* (2013.01); *A61B 5/0531* (2013.01); *A61B 5/6848* (2013.01); *A61B 18/1477* (2013.01); *A61H 39/002* (2013.01); *A61H 99/00* (2013.01); *A61N 1/06* (2013.01); *A61N 1/328* (2013.01); *A61B 2018/0047* (2013.01); *A61B 2018/00875* (2013.01);
(Continued)

(58) Field of Classification Search
USPC .......................................................... 607/116
See application file for complete search history.

(56) References Cited

U.S. PATENT DOCUMENTS

| 2005/0070841 A1 | 3/2005 | Mathiesen et al. |
| 2005/0228249 A1* | 10/2005 | Boling ................ A61B 5/0478 600/378 |
| 2007/0288078 A1* | 12/2007 | Livneh ............... A61B 18/1477 607/147 |

FOREIGN PATENT DOCUMENTS

| JP | 2007-531578 A | 11/2007 |
| JP | 2009-512496 A | 3/2009 |
| KR | 10-0943089 B1 | 2/2010 |

* cited by examiner

*Primary Examiner* — Nicole F Johnson
(74) *Attorney, Agent, or Firm* — McCarter & English, LLP; Steven G. Davis; David R. Burns

(57) ABSTRACT

The present invention relates to a treatment apparatus using high frequency waves, and to a method for controlling same. The treatment apparatus using high frequency waves comprises: a high frequency wave generating unit; a plurality of needles for providing, into the skin of a user, high frequency energy transferred from the high frequency wave generating unit; and a driving unit for inserting the plurality of needles into the skin of the user, wherein the apparatus further comprises a control unit for controlling the driving unit such that the plurality of needles are inserted into a first target point within the skin and then move to a second target point.

15 Claims, 8 Drawing Sheets

(51) Int. Cl.
*A61B 5/04* (2006.01)
*A61N 1/40* (2006.01)
*A61N 1/06* (2006.01)
*A61N 1/32* (2006.01)
*A61B 5/053* (2006.01)
*A61H 39/00* (2006.01)
*A61B 5/00* (2006.01)
*A61H 99/00* (2006.01)
*A61B 18/14* (2006.01)
*A61B 18/00* (2006.01)

(52) U.S. Cl.
CPC ... *A61B 2018/143* (2013.01); *A61B 2562/046* (2013.01); *A61H 2039/005* (2013.01); *A61H 2201/0157* (2013.01); *A61H 2230/655* (2013.01)

(a)

(b)

(c)

(d)

TREATMENT APPARATUS USING HIGH FREQUENCY WAVES AND METHOD FOR CONTROLLING SAME

RELATED APPLICATIONS

This application is a continuation of U.S. Pat. No. 9,364,392, filed on Jan. 24, 2014, which is a 35 U.S.C. §371 National Stage Application of International Application No. PCT/KR2012/005848 filed on Jul. 23, 2012, which claims the benefit of Korean Patent Application No. 10-2011-0074202 filed on Jul. 26, 2011. The entire contents of each of the foregoing applications are explicitly incorporated herein by reference.

TECHNICAL FIELD

The present invention concerns a treatment apparatus using high-frequency waves, and more specifically, to a treatment apparatus using high-frequency waves, which may treat skin tissue using high-frequency energy.

BACKGROUND

There are a wide range of applications of the technology of treating skins by providing energy to skins using various energy sources to deform the skin tissues or enhancing tissue characteristics. Skin treatment apparatuses using a diversity of energy sources such as laser beams, flash lamps, or ultrasonic waves have been being developed, and nowadays, research on skin treatment apparatuses adopting RF waves are intensively underway.

If high-frequency energy is supplied to a skin surface, as the electric current of the high-frequency wave changes its flowing direction, molecules in the skin are rendered to vibrate, causing friction between the molecules. Accordingly, the molecules are rotated, twisted, or collide each other, generating deep heat. Such deep heat raises the temperature of the skin tissue, reorganizing the collagen layer thereby to relieve wrinkles and enforce skin elasticity. Further, blood circulation in the skin tissue can be promoted, contributing to anti-aging or better skin condition.

Korean Patent Application Publication No. 2010-0101420 (published on Sep. 17, 2010) discloses a treatment apparatus using high-frequency waves.

In the treatment apparatus using high-frequency waves, a needle-shaped electrode is inserted into a subcutaneous area to supply high-frequency energy. This treatment apparatus shows different effects depending on the points under user's skin. However, the conventional treatment apparatus has a difficulty in precisely controlling the position where high-frequency energy is supplied. Accordingly, the optimal treatment effects are difficult to bring up depending on the position or details of a surgical procedure.

SUMMARY

The present invention has been designed to address the above-described problems, and an object of the present invention is to provide a treatment apparatus using high-frequency waves that may provide high-frequency energy to various positions under the skin depending on details of a surgical procedure and a method of controlling the same.

The above-described objects of the present invention may be achieved by a treatment device, comprising: a high-frequency wave generating unit; a plurality of needles providing high-frequency energy delivered from the high-frequency wave generating unit to a subcutaneous area; a driving unit providing a driving force for inserting the plurality of needles into the subcutaneous area; and a controller controlling the driving unit to insert ends of the plurality of needles to a first target point in the subcutaneous area and to then shift the ends of the plurality of needles to a second target point. The first target point may be located deeper from a skin surface than the second target point.

The plurality of needles may be configured to provide high-frequency energy to the first target point and shift to the second target point to provide high-frequency energy to the second target point.

The controller may control the driving unit so that the plurality of needles provide high-frequency energy at a fixed position for a predetermined first time at the first target point, and shift to the second target point to provide high-frequency energy at a fixed position for a predetermined time. The first time and the second time each are not less than 0.1 secs and not more than 1 sec.

The plurality of needles may be configured not to provide high-frequency energy at the first target point and to provide high-frequency energy at the second target point.

At this time, the controller may control the driving unit so that when the plurality of needles shift to the second target point, the plurality of needles provide high-frequency energy at a fixed position for a predetermined time. The first target point may be located deeper by not less than 0.5 mm and not more than 3 mm than the second target point.

Meanwhile, the treatment device may further comprise a sensor that may measure an impedance of skin tissue where the ends of the plurality of needles are positioned, wherein the controller may control an output or frequency of high-frequency energy provided through the plurality of needles based on the impedance measured by the sensor.

Specifically, the treatment device may further comprise a plate where the plurality of needles are formed; an interworking unit provided to pressurize a side surface of the plate and enable the plate to move back and forth; and at least one elastic member provided at another side surface to pressurize the plate in an opposite direction of a direction in which the interworking unit pressurizes the plate.

At this time, the elastic member may be arranged along an edge of the plate, and wherein an elasticity modulus of the elastic member at, at least, one position of the edge of the plate may be different from an elasticity modulus at an adjacent position so that the plurality of needles are inserted to the skin surface at an inclined position.

Meanwhile, the above-described objects of the present invention may be achieved by a treatment device, comprising: a high-frequency wave generating unit; a plurality of needles providing high-frequency energy delivered from the high-frequency wave generating unit to a subcutaneous area; and a driving unit providing a driving force for inserting the plurality of needles to the subcutaneous area, wherein ends of the plurality of needles are inserted to a first target point and then the plurality of needles are shifted to a second target point by the driving force controlled by the driving unit.

Or, the objects may be achieved by a method of controlling a treatment device using high-frequency waves, the method comprising: driving a driving unit so that a plurality of needles are inserted to a first target point in a subcutaneous area; delivering first high-frequency energy to the plurality of needles from a high-frequency wave generating unit so that high-frequency energy may be provided to the first target point; driving the driving unit to shift the plurality of needles to the second target point; and delivering second high-frequency energy to the plurality of needles from the high-frequency wave generating unit so that high-frequency energy may be provided to the second target point.

Further, the above-described objects may be also achieved by a treatment method using high-frequency waves, the treatment method comprising: inserting a plurality of needles to a first target point in a subcutaneous area; providing first high-frequency energy to the first target point through ends of the plurality of needles; shifting the plurality of needles to the second target point; and providing second high-frequency energy to the second target point through the ends of the plurality of needles.

The above-described objects may be also achieved by a treatment method using high-frequency waves, the treatment method comprising: inserting a plurality of needles to a first target point in a subcutaneous area; shifting the plurality of needles back to a second target point; and providing high-frequency energy to the second target point through ends of the plurality of needles.

According to the present invention, the position under the skin, to which high-frequency energy is supplied may be controlled, and high-frequency energy is sequentially supplied at different depths from each other, thereby capable of enhancing treatment effects. Further, the conventional issue of being difficult to supply high-frequency energy at a precise depth due to the skin being pressurized by insertion of multiple needles may be addressed by the present invention, which may apply high-frequency energy at a right depth.

DETAILED DESCRIPTION OF EMBODIMENTS

Hereinafter, a high-frequency wave treatment apparatus according to an embodiment of the present invention is described in detail with reference to the accompanying drawings. The relationship in position between components is described based on the drawings. For ease of description, the drawings may be simplified or exaggerated as necessary. Accordingly, the present invention is not limited to the embodiment, and other various devices may be added or changes or omissions may also be made thereto.

Figure 1:
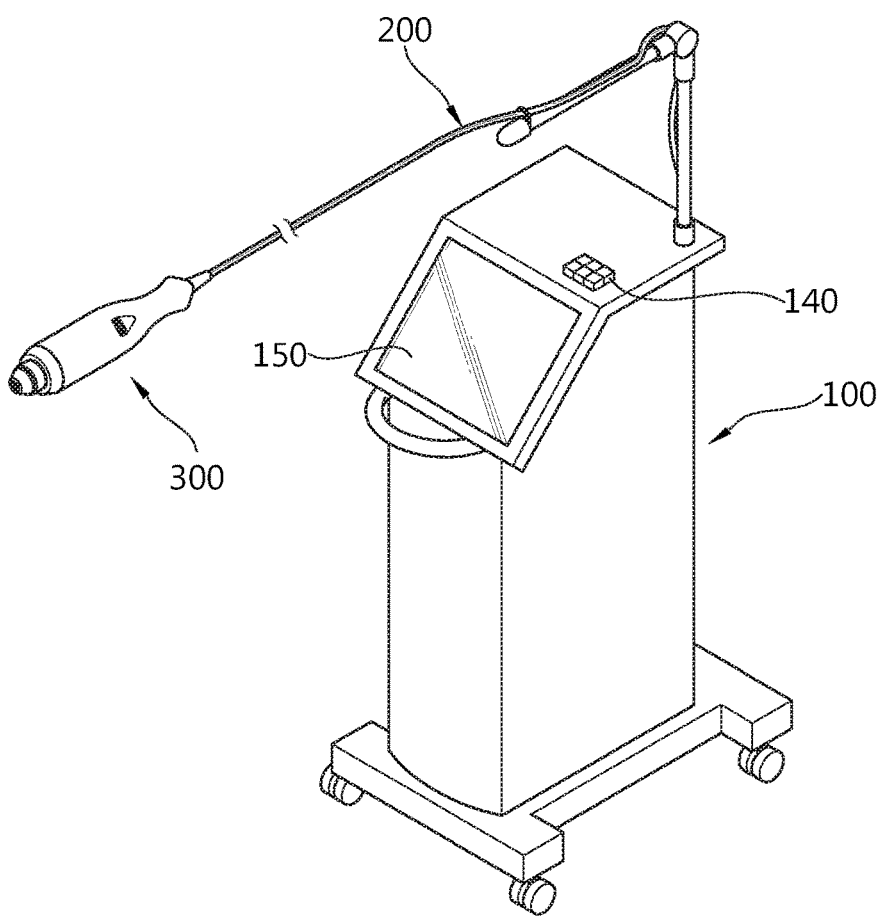
FIG. 1 is a perspective view illustrating a treatment apparatus using high-frequency waves according to an embodiment of the present invention.

FIG. 1 is a perspective view illustrating a treatment apparatus using high-frequency waves according to an embodiment of the present invention. As illustrated in FIG. 1, the high-frequency treatment apparatus includes a main body 100, a hand piece 300, and a cable 200 that connects the main body 100 with the hand piece 300.

The main body 100 includes a power supply (not shown) that may receive power from the outside. On an outer surface of the main body 100 may be provided a control panel 140 for driving what is driven and a display 150 for displaying it to a user. At an inside of the main body 100 is provided a high-frequency wave generating unit 110 that generates high-frequency energy using power supplied from the power supply.

The hand piece 300 includes a body 301 and an electrode unit 310. The body 301 forms the frame of the hand piece 300 and is shaped to be grasped by a user when in use. The electrode unit 310 is formed at an end of the body 301. The electrode unit 310 is electrically connected with the high-frequency wave generating unit 110. Accordingly, upon a surgical procedure, high-frequency energy is supplied to the skin tissue.

Meanwhile, the cable 200 is provided between the main body 100 and the hand piece 300, and may include a high-frequency wave delivering unit 210 and a signal line 220. The high-frequency wave delivering unit 210 electrically connects the high-frequency wave generating unit 110 of the main body 100 with the electrode unit 310 of the hand piece 300 and forms a high-frequency circuit through which high-frequency energy is supplied to the skin tissue. The signal line 220 delivers various control signals or sensing signals between the main body 100 and the hand piece 300. For example, the signal line 220 may deliver a control signal in order for a control unit to control the hand piece 300 or deliver sensing signals measured from various sensors to the control unit.

Figure 2:
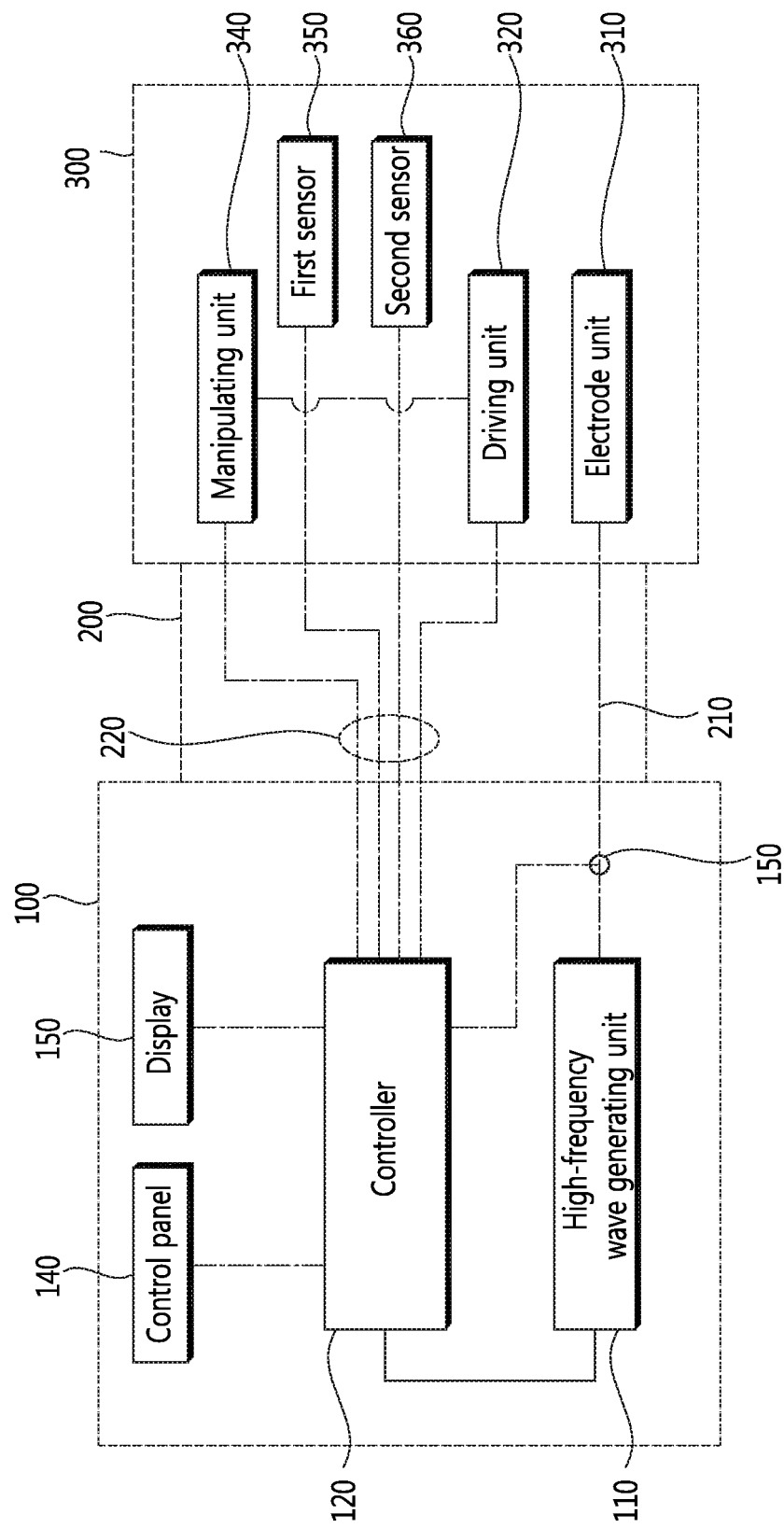
FIG. 2 is a block diagram schematically illustrating the configuration of a treatment apparatus using high-frequency waves, as illustrated in FIG. 1.

FIG. 2 is a block diagram schematically illustrating a treatment apparatus using high-frequency waves as illustrated in FIG. 1. Hereinafter, the connections between the components in the treatment apparatus according to an embodiment of the present invention is described in more detail with reference to FIG. 2.

As described above, the main body 100 includes various components including the control panel 140 that allows a user to set an operation mode of the treatment apparatus using high-frequency waves, the display 150 that displays what is operated in the treatment apparatus and various pieces of information, and the high-frequency wave generating unit 110 that generates high-frequency energy. Further, a control unit 120 is provided which may control the driving of all or some of the components.

For example, when a user sets an operation mode through the control panel 140, operation information on the mode is transmitted to the control unit 120. The control unit 120 controls the high-frequency wave generating unit 110 and other various components so that the components conduct operations corresponding to the set operation mode or an operation mode previously stored in a main processor (not shown). The control unit 120 may display the operation information of the treatment apparatus and information sensed by various sensors on the display 150 to thereby deliver such information to the user.

If an operation mode is set to proceed with a surgical procedure using high-frequency energy, the control unit 120 drives the high-frequency wave generating unit 110 to provide high-frequency energy to the electrode unit 310 of the hand piece 300. In contrast, when the supply of the high-frequency energy should be stopped, the control unit 120 may stop driving the high-frequency wave generating unit 110 or control a circuit device such as a relay device 150 positioned over a path along which the high-frequency energy is delivered so that the high-frequency energy is stopped from being delivered to the hand piece.

Meanwhile, the hand piece 300 includes the electrode unit 310, a driving unit 320 for moving the position of the electrode unit 310, and a manipulating unit 340 for manipulating the driving of the hand piece. The hand piece 300 may further include a first sensor 350 for sensing the position of the electrode unit and a second sensor 360 for measuring the impedance of the skin where a surgical procedure proceeds.

As illustrated in FIG. 2, the electrode unit 310 is electrically connected with the high-frequency wave generating unit 110 by the high-frequency wave delivering unit 210 of the cable 200. Accordingly, the high-frequency energy delivered from the high-frequency wave generating unit 110 upon a surgical procedure may be provided to a subcutaneous area. At this time, some components of the electrode unit 310 are provided to be selectively inserted into the subcutaneous area, so that high-frequency energy may be provided to the subcutaneous area. The driving unit 320 is provided at a side of the electrode unit 310 to thereby provide a driving force that enables some components of the electrode unit 310 to be inserted into the subcutaneous area.

The electrode unit 310 and the driving unit 320 are connected with the control unit 120 via the signal line 220 of the cable 200. Accordingly, the control unit 120 may control the driving of the driving unit 320 and the electrode unit 310 to correspond to an operation mode previously stored in the main processor or an operation mode set by a user.

Meanwhile, as described above, the hand piece 300 may have a separate manipulating unit 340. Accordingly, a user may manipulate what is driven by the driving unit 320 and the electrode unit 310 in a brief way through the manipulating unit 340, while holding the hand piece 300 upon a surgical procedure.

Further, the manipulating unit 340 is connected with the electrode unit 310, so that during the course of a surgical procedure, the manipulating unit 340 may deliver what is manipulated by a user to the control unit 120. Further, the control unit 120, in case a mode where no surgical procedure is conducted is set, may enable the hand piece 300 to be not able to be manipulated through the manipulating unit 340.

The first sensor 350 and the second sensor 360 of the hand piece 300 are connected with the control unit 120 of the body 100 and transmit sensed information to the control unit 120. The control unit 120 may control the operation of each component, with the information sensed from the first sensor 350 and the second sensor 360 reflected.

Figure 3:
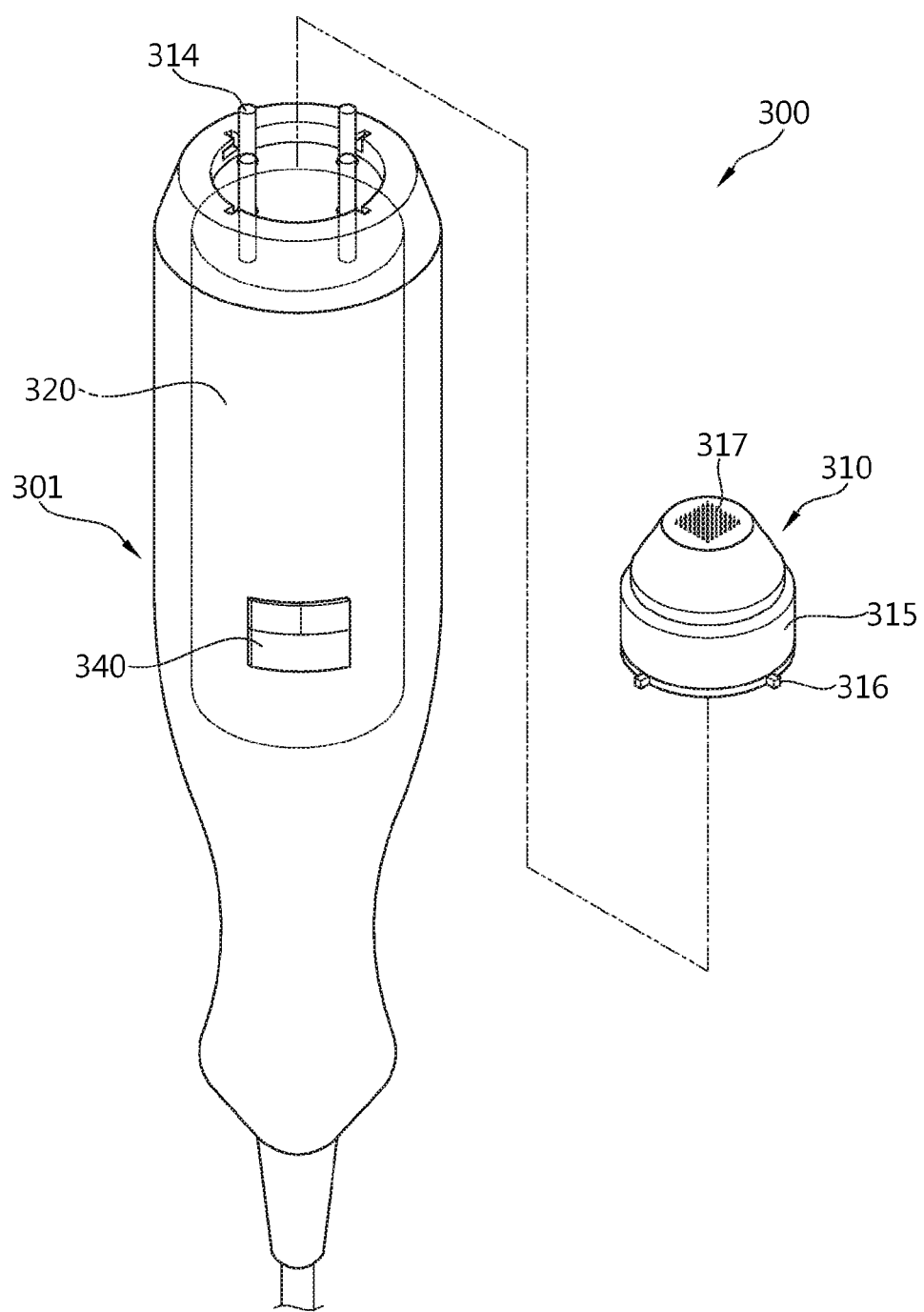
FIG. 3 is a perspective view illustrating a hand piece as illustrated in FIG. 1.
Figure 4:
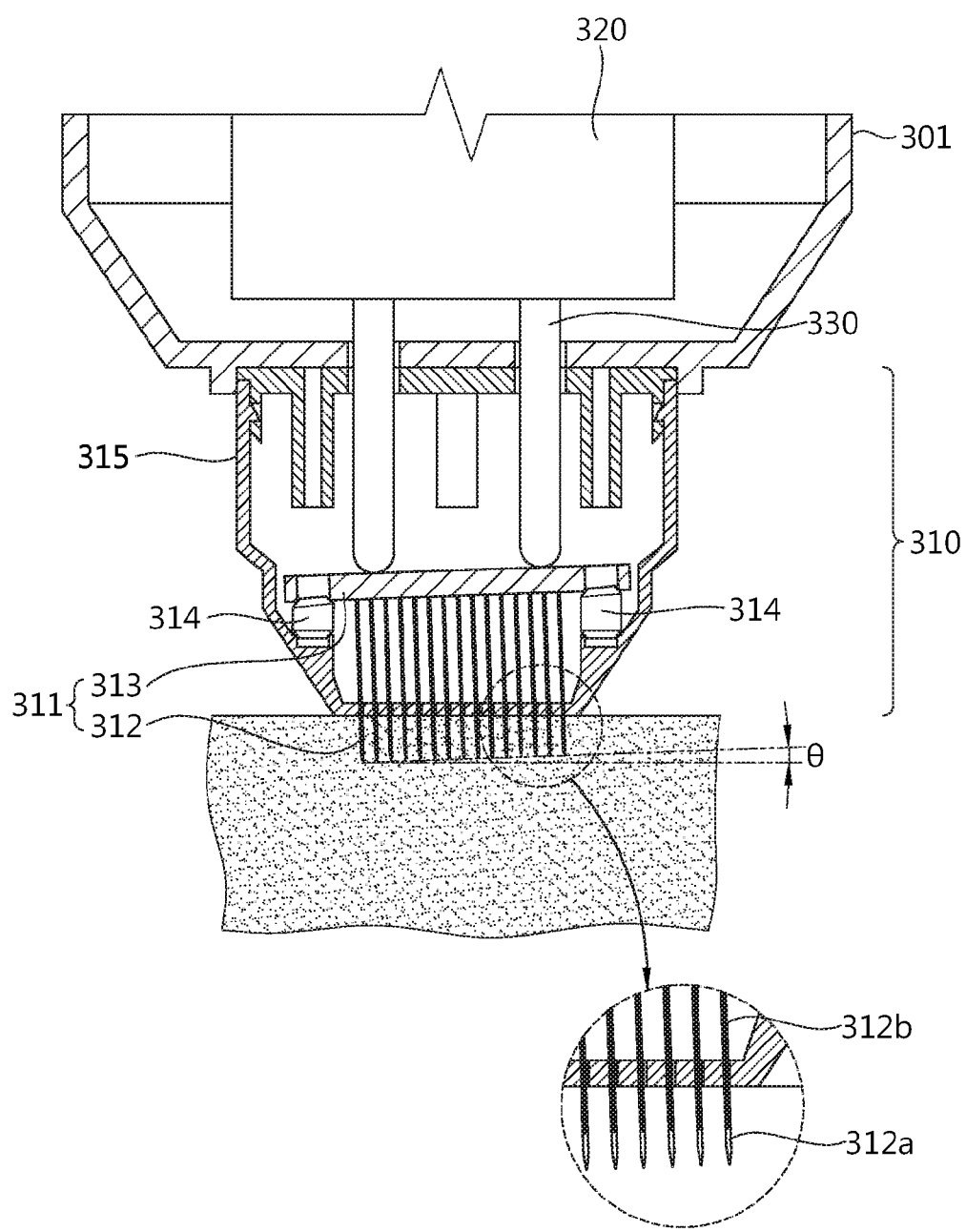
FIG. 4 is a cross-sectional view illustrating the structure of a cross section of an end of a hand piece as illustrated in FIG. 3.

FIG. 3 is a perspective view illustrating a hand piece as illustrated in FIG. 1, and FIG. 4 is a cross-sectional view illustrating an end of a hand piece as illustrated in FIG. 3. Hereinafter, the configuration of a hand piece is described in greater detail with reference to FIGS. 3 and 4.

The hand piece 300 includes a body 301 and an electrode unit 310 provided at an end of the body 301. As illustrated in FIG. 3, the electrode unit 310 is detachably provided with at least one detachable protrusion 316 at an outer side thereof. Accordingly, a user may select and use a proper one of multiple electrode units 310 having various structures depending on surgical procedures and may frequently exchange the electrode units 310 considering sanitary issues.

At an outer surface of the body is provided the manipulating unit 340 that may control the operation of the hand piece 300. The manipulating unit 340, as described above, is connected with the driving unit 320 and the electrode unit 310 to transmit a control signals, and is further provided to transmit/receive control signals to/from the control unit 120 of the body 100.

As illustrated in FIG. 2, a driving unit 320 is provided at an inner side of the body 301. At an end of the driving unit 320 is provided an interworking unit 330 that is shaped as multiple bars and may pressurize some components of the electrode unit. Accordingly, the driving unit 320 makes the interworking unit 330 move back and forth, thereby delivering a driving force that allows the electrode unit 310 to be inserted into the subcutaneous area. The driving unit 320 may be configured using a solenoid, a step motor, and a linear motor in various manners.

As illustrated in FIG. 4, the electrode unit 310 includes a case 315 for forming its outer look and an electrode module 311 that is provided at the inside of the case 315. As described earlier, at least one or more detachable protrusions 316 are provided at an outer circumferential surface of the case 315. At a front side, a plurality of through holes 317 are formed.

The electrode module 311 includes a plurality of needles 312 and a plate 313 where the needles 312 are provided. The plate 313, although not specifically shown in the drawings, is electrically connected with the high-frequency wave generating unit 110 of the body 100. Accordingly, the high-frequency energy delivered from the high-frequency wave generating unit 110 is provided to the plurality of needles 312 through an electric circuit provided in the plate 313.

The plurality of needles 312 are provided to be able to move in and out of the plurality of through holes 317. The plurality of needles 312 each have a thin and sharp end that facilitates inserting the skin. The diameter of the cross section of the needle's end may be 50 μm or less, and in the instant embodiment, the diameter may be in a range from 15 μm to 30 μm.

At this time, the plurality of needles 312 may be configured to provide high-frequency energy through the ends 312a of the needles with the needles inserted into the skin. Accordingly, the surface of the end 312a of each needle is formed of a conductive material, and the surface of the other portion than the needle end 312a is formed of an insulating material. As such, the portion of each needle 312, where high-frequency energy is delivered does not exceed 0.5 mm from the tip of the needle 312, and in this embodiment, high-frequency energy is delivered in a range 312a that is within 0.3 mm from the tip of the needle.

The position of the electrode module 311 is varied as the interworking unit 330 is rendered to move back and forth by driving the driving unit 320. As illustrated in FIG. 4, an end of the interworking unit 330, when the interworking unit 330 moves along a straight line, is provided to move in and out of the inside of the case 315 through a rear surface of the case 315. Accordingly, as the interworking unit 330 moves forwards, it pressurizes a side of the plate 313 of the electrode module 311, and the needles 312 of the electrode module 311 travel toward through the through holes of the case, penetrate into the skin, and are then inserted into the subcutaneous area.

As illustrated in FIG. 4, at another side of the plate 313 is formed at least one elastic member 314. The elastic member 314 pressurizes the plate 313 in an opposite direction of the direction along which the interworking unit 330 pressurizes the plate. Accordingly, if the driving unit 320 is driven to make the interworking unit 330 advance, the electrode module 311 moves forwards, and the elastic member 314 is contracted. If the driving unit 320 is driven to move the interworking unit 330 backwards, the electrode module 311 is rendered to move backwards by the restoring force of the elastic member 314.

The electrode module 311 according to this embodiment has multiple elastic members 314 arranged along the edge of the plate 313. At this time, at least one of the multiple elastic member 314 may be formed to have a different elasticity modulus from that of its adjacent elastic member 314. Accordingly, in case the plurality of needles 312 are inserted into the skin, the plurality of needles 312 sequentially pass through the skin with the electrode module 311 inclined. Accordingly, the pain a patient feels when taking a surgical procedure may be effectively reduced. In this embodiment, multiple elastic members 314 are used. However, one elastic member with different elasticity moduli at different positions, respectively, may be used, and other various structures may be adopted to have multiple needles penetrate into the skin at an inclined position.

Meanwhile, the treatment apparatus using high-frequency waves according to this embodiment is configured to control the position in the subcutaneous area, where high-frequency energy is provided. The skin has stacked layers of tissue, which have different characteristics depending on the depth. Accordingly, there may be different optimal positions where high-frequency energy is to be provided, depending on the purposes of surgical procedures. In the present invention, the insertion depths of needle ends are controlled with the needles 312 inserted into the skin, so that high-frequency energy may be provided at the optimal position depending on the purpose of the surgical procedure and skin characteristics of the patient.

Further, in the present invention, the insertion depths of the needle ends are controlled so that high-frequency energy may be provided at multiple target points. That is, unlike the conventional art, high-frequency energy may be stereoscopically provided to the skin tissue, thus maximizing the effect of a surgical procedure.

Specifically, the depths in which the multiple needles 312 are inserted are determined by the operation of the driving unit 320. For example, if the driving unit 320 moves the interworking unit 330 forwards, the needles 312 are inserted into the skin by the distance of travel of the interworking unit 330. On the contrary, if the driving unit 320 moves the interworking unit 330 backwards, the needles 312 are rendered to move back from the subcutaneous area to the skin surface by the distance of regress of the interworking unit 330, thereby adjusting the depth.

At this time, the operation of the driving unit 320 may be controlled by the control unit 120. The control unit 120 sequentially operates the driving unit 320 according to a set operation mode so that the positions of the needles 312 are sequentially moved to multiple target points.

Here, the hand piece 300 may have a first sensor 350 for measuring the depth of insertion of the needle 312 into the skin. The first sensor 350 may measure the distance of insertion of the needles 312 into the skin based on the distance of travel of the interworking unit 330 or the multiple needles 312. Besides, various measuring methods may apply, of course.

Information on the depth measured by the first sensor 350 is transmitted to the control unit 120. The control unit 120 may adjust the positions of the needles' ends by controlling the driving unit 320 while grasping the positions where the needles 312 are inserted, using the depth information.

Further, the control unit 120, if determining that the end 312a of the needle reaches a preset target point, may deliver high-frequency energy from the high-frequency wave generating unit 110 to the target point.

At this time, the skin tissue has different characteristics at different target points, and thus, control may be conducted to provide high-frequency energy appropriate for the characteristics of skin tissue. In this embodiment, the hand piece 300 further includes a second sensor 360 that senses impedance of the skin tissue where the needle end 312a is positioned. The control unit 120 may control the output value and frequency characteristics of high-frequency energy provided to the target point considering the skin tissue information sensed by the second sensor 360.

Here, the second sensor 360 may be separately provided at the end 312a of the needle or may be configured to measure the impedance of the skin tissue by having a relatively weak current flow through the needles 312.

Figure 5:
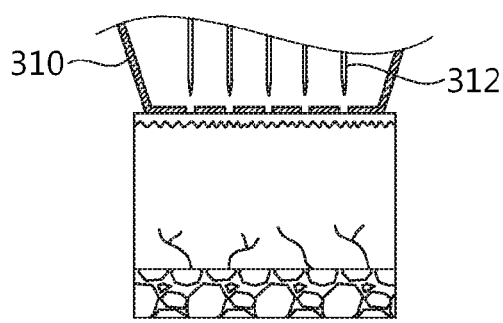
FIG. 5 is a cross-sectional view illustrating an example cross section of the skin where a surgical procedure is performed by a treatment apparatus using high-frequency waves, as illustrated in FIG. 1.
Figure 5:
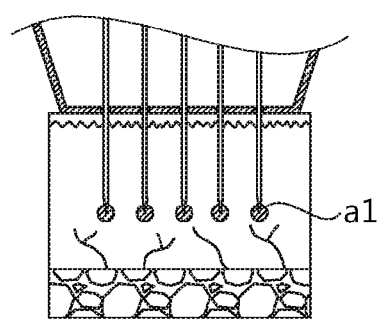
Figure 5:
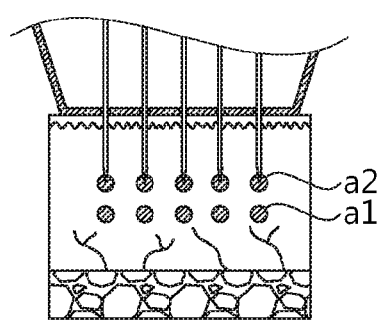
Figure 5:
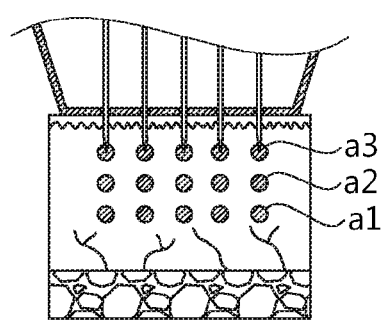
Figure 6:
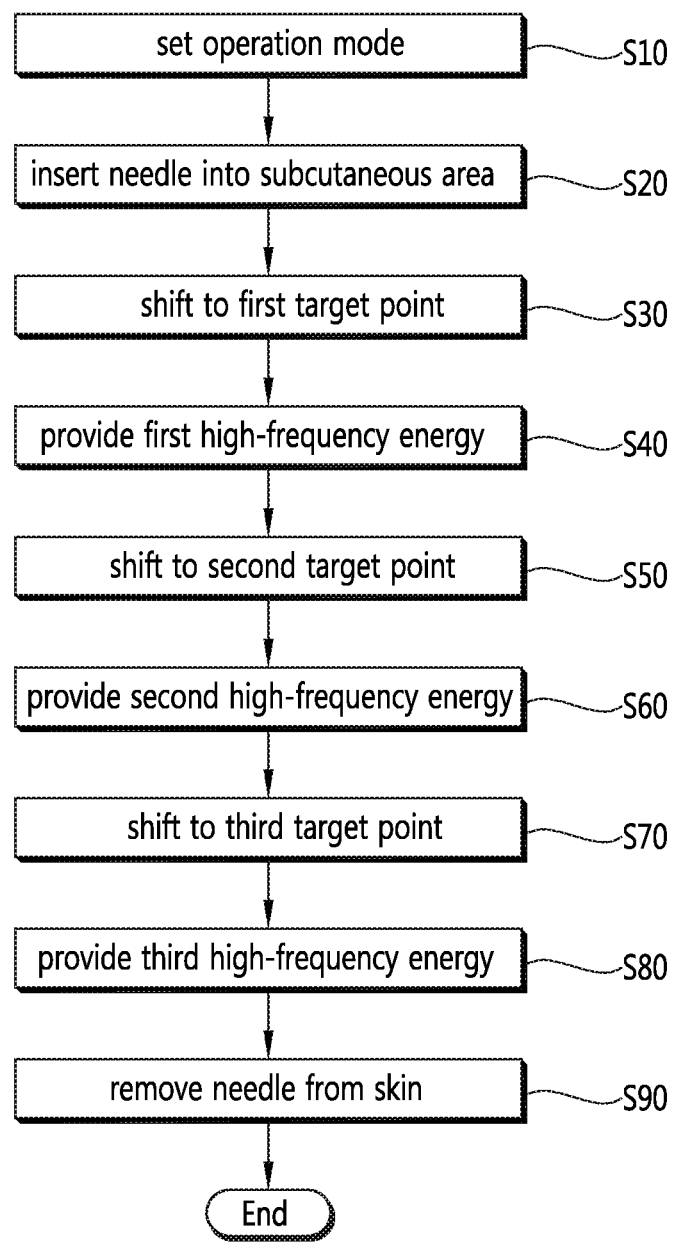
FIG. 6 is a flowchart illustrating a first applicable example of a method of controlling a treatment apparatus using high-frequency waves, as illustrated in FIG. 1.

FIG. 5 is a cross-sectional view illustrating an example cross section of the skin where a surgical procedure is performed using a treatment apparatus as illustrated in FIG. 1. FIG. 6 is a flowchart illustrating a first applicable example of a method of controlling a treatment apparatus using high-frequency waves, as illustrated in FIG. 1. An example method of controlling a treatment apparatus using high frequency waves according to an embodiment of the present invention is described in detail with reference to FIGS. 5 and 6.

First, a user sets an operation mode of the treatment apparatus through the control panel (S10). What is operated in the operation mode may be set so that when the user selects a specific surgical procedure, the operation is performed per a manual stored in the main processor or may be set in such a way that the user individually enters details of the surgical procedure, such as, for example, a first target point, second target point, or output of high-frequency energy.

If the operation mode is set, the user brings the electrode unit 310 of the hand piece 300 in contact with a patient's skin where a surgical procedure is to be carried out (refer to a of FIG. 5). The user starts operation by manipulating the manipulating unit 340.

If the operation starts, the control unit (or manipulating unit) transmits a control signal to the driving unit 320 to drive the driving unit 320. Accordingly, the ends 312a of the plurality of needles pass through the skin (S20) and are inserted through the skin to the first target point a1 (S30, refer to b of FIG. 5). The control unit 120 may block high-frequency energy from being supplied through the needle ends 312a while the needles 312 are being inserted.

Specifically, the interworking unit 330 pressurizes the rear surface of the plate 313 where the needles 312 are formed by the driving of the driving unit 320, and the needles 312 are rendered to project through the through holes 317, penetrating into the skin. At this time, since the plate 313 has multiple elastic members 314 having different elasticity moduli formed at a front side thereof, the plurality of needles may be inserted into the skin at an inclined position.

The driving unit 320 continues to operate thereby moving the plurality of needle ends 312a to the first target point a1. At this time, the control unit 120 may locate the needles to the first target point a1 by driving the driving unit 320 for a predetermined time corresponding to the first target point a1. Or, the needle ends 312a may be located to the first target point a1 using the information provided from the first sensor 350.

Meanwhile, if the needle ends 312a are located at the first target point a1, the control unit 120 provides first high-frequency energy to the first target point a1 (S40). While the first high-frequency energy is provided, the driving unit 320 may maintain the stop state for a first time so that the needle ends 312a stay at the first target point a1. Here, the first time may be 0.1 secs or more and 1 sec or less.

The first high-frequency energy may be determined by the user when setting the operation mode or by a value previously stored in the main processor. Or, the second sensor 360 measures the impedance of the first target point a1 and the control unit 120 may select the output or frequency to correspond to the impedance and may provide the output or frequency to the first target point a1.

If the step of providing the first high-frequency energy is complete, the control unit 120 blocks high-frequency energy from being provided from the needle ends and drives the driving unit 320 to move the plurality of needle ends 312a to the second target point a2 (S50, refer to c of FIG. 5). At this time, as illustrated in FIG. 5, the second target point a2 may be located closer to the skin surface than the first target point a1. Accordingly, the driving unit 320 is controlled to be driven in the direction in which the interworking unit 330 recesses, unlike when moving to the first target point a1. Thus, the plate 313 of the electrode module is pressurized by the plurality of elastic members and is thus rendered to shift back by the distance of recess of the interworking unit 330, and the needle ends 312a are relocated to the second target point a2.

Here, whether the control unit 120 has relocated the needle ends 312a to the second target point a2 may be determined in a similar way to when locating the needle ends 312a to the first target point a1.

If the plurality of needle ends 312a are relocated to the second target point a2, second high-frequency energy is provided to the second target point a2 (S60). Upon supply of the second high-frequency energy, the driving unit 320 may maintain the stop state for a second time. Here, the second time may be 0.1 secs or more and 1 sect or less.

Here, the characteristics of the second high-frequency energy provided to the second target point a2 may be determined in a similar way to determining the characteristics of the first high-frequency energy as described above.

Meanwhile, if the step of providing the second high-frequency energy is complete, the control unit 120 blocks the high-frequency energy from being provided from the needle ends 312a and drives the driving unit 320 to relocate the plurality of needle ends 312a to a third target point a3 (S70, refer to d of FIG. 5). As illustrated in FIG. 5, the third target point a3 is located closer to the skin surface than the second target point a2. The driving unit 320 may relocate the needle ends 312a to the third target point a3 by additionally moving the interworking unit 330 back.

Here, whether the control unit 120 has relocated the needle ends 312a to the third target point a3 may be determined in a similar way to when relocating the needle ends 312a to the first target point a1 or second target point a2.

If the plurality of needle ends are relocated to the third target point a3, third high-frequency energy is supplied to the third target point a3 (S80). When the third high-frequency energy is supplied, the driving unit 320 may maintain the stop state for a third time. Here, the third time may be not less than 0.1 secs and not more than 0.1.

Here, the characteristics of the third high-frequency energy provided to the third target point a3 may be determined in a similar way to when determining the characteristics of the first high-frequency energy and second high-frequency energy as described above.

If the step of providing the third high-frequency energy is performed and the necessary surgical procedure is complete, the driving unit 320 drives the interworking unit 330 in a direction in which the interworking unit 330 moves back, thereby completely removing the plurality of needles 312 from the skin (S90). Accordingly, the surgical procedure at the position is complete, and the position where the surgical procedure is performed is changed to another position, where a surgical procedure is conducted repeatedly in a similar way.

In this embodiment, rather than high-frequency energy being supplied only to a specific depth at the position where a surgical procedure is underway, high-frequency energy may be provided at a plurality of target points with the needles inserted into the skin. At this time, considering the range in which high-frequency energy is expanded to the skin tissue, a difference in depth between the first target point and the second target point and a difference in depth between the second target point and the third target point may be set to be not less than 0.5 mm and not more than 3 mm. In such case, high-frequency energy may be stereoscopically provided into the subcutaneous area, so that the effect of the surgical procedure can be significantly enhanced.

In the instant embodiment, high-frequency energy is sequentially provided from the first target point to the third target point, while moving from the deepest position from the skin surface to a position relatively closer to the skin. However, the present invention is not limited to such order of depth, and the surgical procedure can be performed with the positions changed.

However, in case a surgical procedure is sequentially performed from the deepest target point, the tissue can be prevented from being damaged by the needles in the state where high-frequency energy is provided so that the skin tissue starts to be deformed, and an error in grasping the positions of the needle ends, which may occur due to the skin being pressurized by insertion of the needles, may be minimized.

Further, in the above embodiment, high-frequency energy is provided to three target points depending on the depths of the positions where the surgical procedure is conducted. However, this is merely an example, and two or four or more target points may be set depending on depths, and high-frequency energy may be provided to the set target points.

Figure 7:
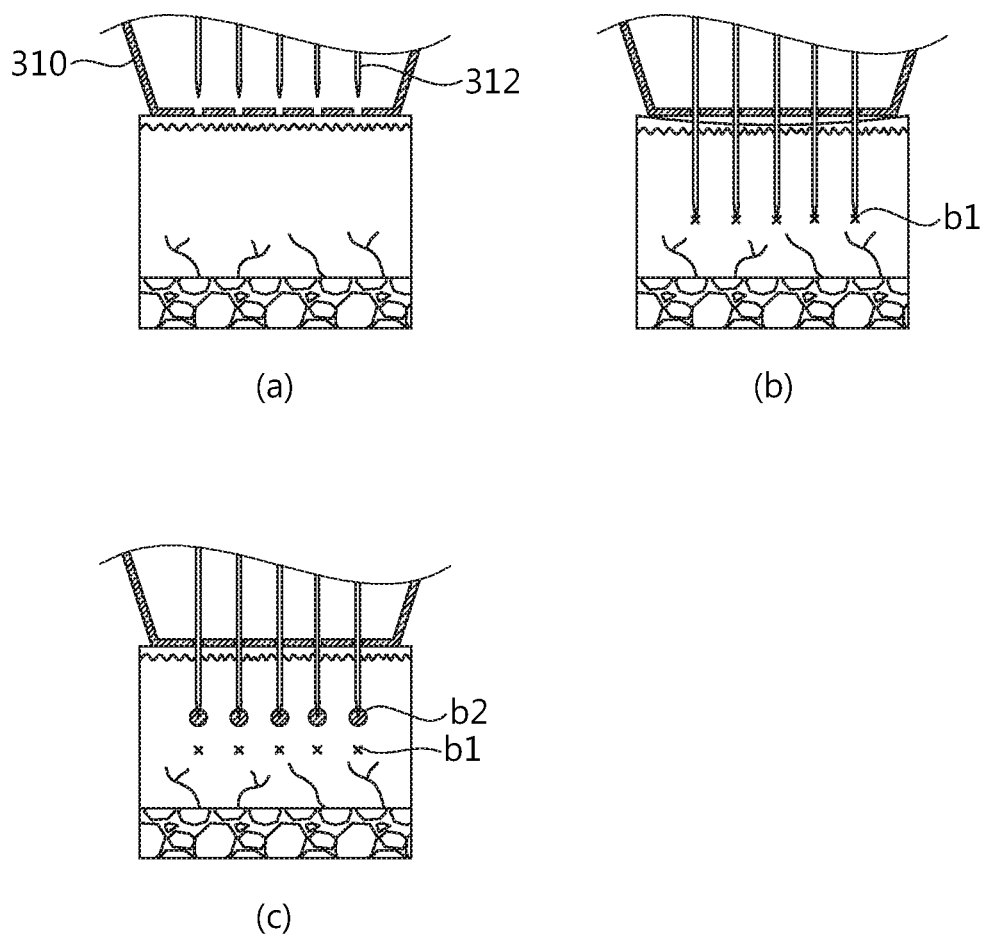
FIG. 7 is a cross-sectional view illustrating another example cross section of the skin where a surgical procedure is performed by a treatment apparatus using high-frequency waves, as illustrated in FIG. 1.
Figure 8:
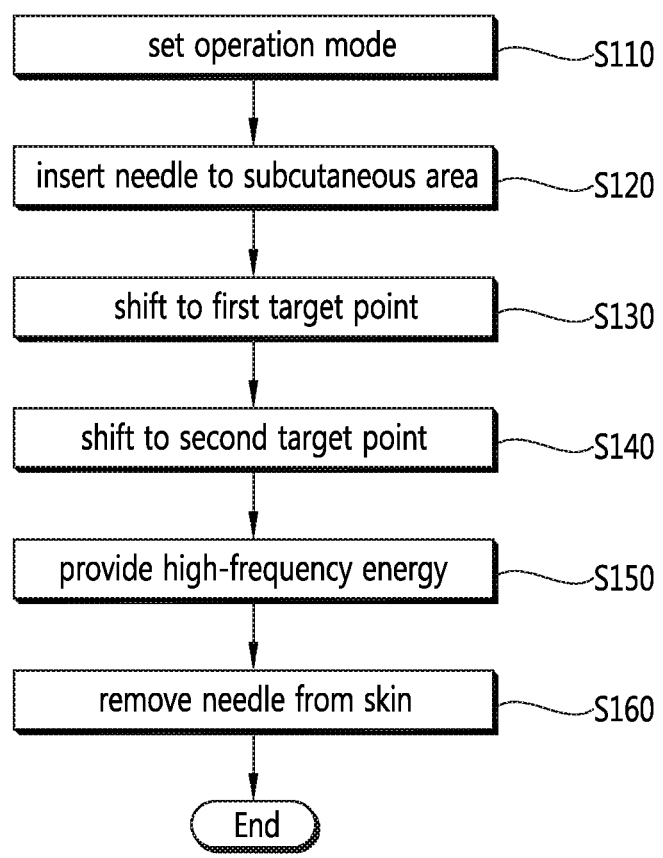
FIG. 8 is a flowchart illustrating a second applicable example of a method of controlling a treatment apparatus using high-frequency waves, as illustrated in FIG. 1.

FIG. 7 is a cross-sectional view illustrating another example cross section of the skin where a surgical procedure is conducted by a treatment apparatus using high-frequency waves, as illustrated in FIG. 1, and FIG. 8 is a flowchart illustrating a second applicable example of a method of controlling a treatment apparatus using high-frequency waves, as illustrated in FIG. 1. Hereinafter, a method of controlling a treatment apparatus using high-frequency waves according to another embodiment of the present invention is described in detail with reference to FIGS. 7 and 8. However, what is similar to the above-described control method is not repeated described.

As in the present invention, when invasive needles are inserted into the skin and a surgical procedure is performed, the needles pressurize the skin in the travelling direction when inserted, and thus, the skin may be pushed to the subcutaneous area when the needles are inserted. Accordingly, when providing high-frequency energy at a specific position of the skin tissue using the needs, the needles may be difficult to locate to the specific position.

The present invention is configured so that the positions of the needle ends 312a are controlled with the needles 312 inserted into the skin. The needles 312 are inserted down to the first target point b1 that is located deeper than the second target point b2 where high-frequency energy is to be provided, and the needles 312 are then moved back to the second target point b2, thereby minimizing an error that may occur due to the skin being pushed down.

Specifically, in case a user intends to provide high-frequency energy to the second target point b2, the user sets a corresponding operation mode (S110). At this time, the user may directly input the first target point b1 and the second target point b2, or if the user selects a mode for designating the second target point b2, the control unit itself may determine the first target point b1 and set the operation mode.

If the operation mode is set, the user brings the electrode unit 310 of the hand piece 300 in contact with a patient's skin surface where a surgical procedure is to be conducted (refer to a of FIG. 7). The user then manipulates the manipulating unit 340 to start operation. If the operation is started, the control unit (or manipulating unit) transmits a control signal to the driving unit 320 to drive the driving unit 320. Accordingly, the plurality of needle ends 312a pass through the skin (S120) and are inserted to the first target point b1 in the subcutaneous area (S130). The control unit 120 may block high-frequency energy from being supplied through the needle ends 312a while the needles 312 are being inserted.

As illustrated in b of FIG. 7, while the needles are being inserted to the first target point b1, the skin stays pressurized in the travelling direction of the needles 312. As described above, as a method of the control unit 120 controlling the positions of the needles 312, the driving unit 320 is driven for a predetermined time, or based on the travelling distance of the interworking unit 330 or needles 312, the positions of the needle ends 312a are determined. Accordingly, in the state shown in a of FIG. 7, the needle ends are located at the position d2 that is shallower that the depth d1 that is actually targeted by the control unit.

Meanwhile, the control unit 120 may control the driving unit so that the plurality of needles regress to the second target point b2 with the needles 312 inserted to the first target point b1 (S140). As illustrated in c of FIG. 7, since the plurality of needles 312 travel to the skin surface when moved to the second target point b2, the skin surface is moved along with the needles 312 so that the above-described phenomenon that the skin is pushed down may be released. Accordingly, when the plurality of needles 312 are located at the second target point b2, the depth targeted by the control unit 120 may be substantially the same as the actual depth of insertion of the needles 312.

Accordingly, the control unit 120 provides high-frequency energy through the high-frequency wave generating unit 110 with the plurality of needles 312 located at the second target point b2 (S150). In such case, high-frequency energy may be precisely provided at the target point set by the user.

If the step of providing high-frequency energy is complete, the control unit 120 additionally moves back the needles 312, thereby completely removing the needles 312 from the skin (S90). Accordingly, if the surgical procedure is terminated at the position, a shift is made to another position where the surgical procedure is then repeated in a similar way.

As such, in the instant control method, needles inserted deeper than a target point where high-frequency energy is to be provided, and the needles are then moved back to the target point, thereby minimizing an error in insertion depth that may occur as the skin is pressurized upon an invasive surgical procedure. At this time, the depth in which the needles are initially inserted may be larger by 0.5 mm or more and 3 mm or less than the target point where high-frequency energy is supposed to be provided.

In the above embodiment, upon a surgical procedure, high-frequency energy is provided at a target point in the subcutaneous area. However, like in the above-described embodiment, the same method may apply even when high-frequency energy is to be provided to multiple target points, by inserting the needles deeper than the target point where high-frequency energy is supposed to be provided upon initial insertion.

As such, the present invention provides a treatment apparatus using high-frequency waves, which may control the positions of the needles while the needles inserted into the skin. Accordingly, high-frequency energy may be provided to multiple target points, and thus, a surgical procedure may be stereoscopically performed. Further, an error may be minimized which may arise when the skin is pressurized upon an invasive surgical procedure.

Although embodiments of the present invention have been described, it is to be understood by one of ordinary skill in the art that various changes in form and detail may be made thereto without departing from the scope of the invention as defined by the following claims.

What is claimed is:

1. A treatment method using RF treatment apparatus, the treatment method comprising:
    inserting a plurality of needles to a first depth in a subcutaneous area;
    providing RF energy to the first depth of the subcutaneous area through ends of the plurality of needles;
    terminating RF energy delivery to the first depth;
    locating the ends of the plurality of needles to a second depth in the subcutaneous area; and,
    providing RF energy to the second depth of the subcutaneous area through the ends of the plurality of needles.

2. The treatment method of claim 1, wherein the first depth is located deeper from a skin surface than the second depth.

3. The treatment method of claim 2, wherein the first depth is located deeper by not less than 0.1 mm and not more than 3 mm than the second depth.

4. The treatment method of claim 1, wherein in the step for providing RF energy to the first depth the ends of the plurality of needles are stationary at the first depth and RF energy is provided for a predetermined first time, and
    wherein in the step for provided RF energy to the second depth the end of the plurality of needles are stationary at the second depth and RF energy is provided for a predetermined second time.

5. The treatment method of claim 4, wherein the predetermined first time and the predetermined second time are not less than 0.001 secs and not more than 2 secs.

6. The treatment method of claim 1, wherein electrodes for providing RF energy into the subcutaneous area are provided at the ends of the plurality of needles, and surfaces of portions other than the ends are formed of an insulating material.

7. The treatment method of claim 1, wherein a length of portions for providing RF energy are not less than 1 mm from the ends of the needles.

8. The treatment method of claim 1, the treatment method further comprising a step for resting for a predetermined period without providing RF energy into the subcutaneous area between the step for providing RF energy to the first depth and the step for providing RF energy to the second depth.

9. The treatment method of claim 1, wherein during the step for providing RF energy to the first depth or the step for providing RF energy to the second depth, the impedance of a portion where the ends of the plurality of the needle are located is measured and parameters of RF energy are controlled based on the measured impedance.

10. The treatment method of claim 1, wherein in the step for inserting the plurality of needles to the first depth, the end of the plurality of needles are inserted into a portion deeper than the first depth, and moved back to the first depth.

11. A treatment method for treating skin tissue by inserting a plurality needles including at least one electrode into a subcutaneous area and providing RF energy through the electrode, the treatment method comprising:
    providing RF energy at a first depth of the subcutaneous area;
    terminating a treatment for the first depth by stopping providing RF energy to the first depth; and
    providing RF energy at a second depth of the subcutaneous area.

12. The treatment method of claim 11, wherein the first depth is located deeper from a skin surface than the second depth.

13. The treatment method of claim 12, wherein the first depth is located deeper by not less than 0.1 mm and not more than 3 mm than the second depth.

14. The treatment method of claim 11, the treatment method further comprising a step for resting for a predetermined period without providing RF energy into the subcutaneous area between the step for providing RF energy to the first depth and the step for providing RF energy to the second depth.

15. The treatment method of claim 11, wherein electrodes for providing RF energy into the subcutaneous area are provided at the ends of the plurality of needles, and surfaces of portions other than the ends are formed of an insulating material.

* * * * *